United States Patent [19]

Laanen et al.

[11] Patent Number: 4,865,027

[45] Date of Patent: Sep. 12, 1989

[54] NON-REBREATHING COLLAPSIBLE CHAMBER CONTINUOUS AEROSOL DELIVERY SYSTEM WITH INFUSION PORT

[75] Inventors: Craig Laanen, Whitmore Lake; Frank W. Moler, Ann Arbor, both of Mich.

[73] Assignee: The University of Michigan, Ann Arbor, Mich.

[21] Appl. No.: 249,847

[22] Filed: Sep. 27, 1988

[51] Int. Cl.$^4$ .................... A61M 11/00; A61M 15/00; A61M 16/00
[52] U.S. Cl. .................... 128/200.21; 128/203.12; 128/203.29
[58] Field of Search .................... 128/200.14, 200.21, 128/203.12, 203.13, 203.29, 204.11, 204.14, 203.14, 203.19, 203.28, 204.18, 205.13, 205.22, 205.25, 200.15, 200.16, 200.17, 200.18, 200.19, 200.22, 200.23, 203.16, 203.17, 203.19, 204.25

[56] References Cited

U.S. PATENT DOCUMENTS

| | | | |
|---|---|---|---|
| 1,693,730 | 12/1928 | Schröder | 128/203.13 |
| 3,815,596 | 6/1974 | Keener et al. | 128/205.25 |
| 4,098,271 | 7/1978 | Maddock | 128/205.13 |
| 4,440,163 | 4/1984 | Spergel | 128/205.13 |

FOREIGN PATENT DOCUMENTS 18598 of 1911 United Kingdom ........... 128/200.22

*Primary Examiner*—Edgar S. Burr
*Assistant Examiner*—Kimberly L. Asher
*Attorney, Agent, or Firm*—Rohm & Monsanto

[57] ABSTRACT

A therapeutic respiratory apparatus is used to provide a continuous dosage of an aerosolized medicament to a patient. Pressurized carrier gas, which may be a mixture of oxygen and air, is supplied to a nebulizer which contains a reservoir of the liquid medicament. The aerosolized medicament is then delivered to a collapsible chamber which serves to store the aerosol between inhalations by the patient. Upon inhalation, the peak demand for the aerosolized mixture is drawn from the collapsible chamber, which is caused to collapse, so as to be reduced in its volume. A one-way valve prevents gas exhaled by the patient from being urged into the collapsible chamber. The exhalation gas is vented into the ambient air via exhaust valves in a mask, which may be an oxygen mask, coupled to the collapsible chamber. Replenishment of the medicament reservoir in the nebulizer is achieved via an infusion port which may be installed either through the wall of the nebulizer, or through the wall of the collapsible chamber, in the vicinity of the inlet thereof coupled to the nebulizer.

12 Claims, 1 Drawing Sheet

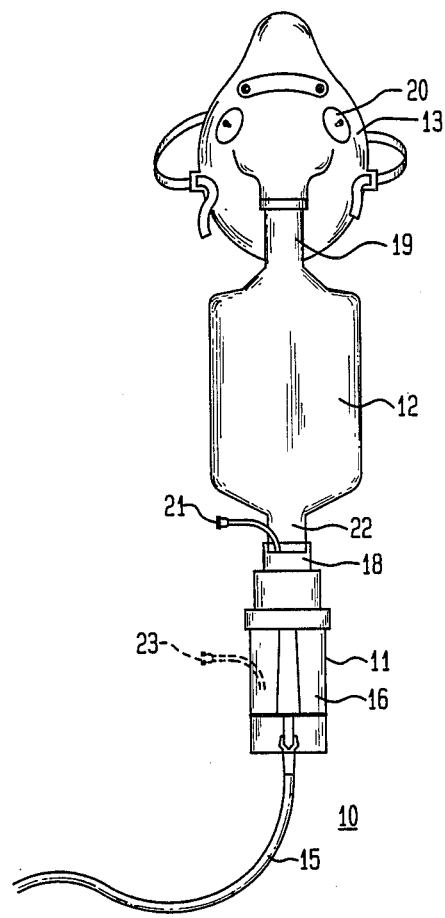

NON-REBREATHING COLLAPSIBLE CHAMBER CONTINUOUS AEROSOL DELIVERY SYSTEM WITH INFUSION PORT

BACKGROUND OF THE INVENTION

This invention relates generally to devices for facilitating respiratory therapy, and more particularly, to an arrangement for delivering a continuous dosage of aerosolized drugs to a patient.

Respiratory inhaling devices, such as gas delivery systems which employ nebulizers, have been utilized for treating various respiratory ailments which range from common colds to complex infections of the bronchial system. Such respiratory therapeutic devices are used in the treatment of ailments which afflict adults and children, notwithstanding that the ailments may be curable and are not serious. One significant benefit of the respiratory devices is the minimizing of relatively high levels of discomfort which are associated with most respiratory ailments.

It is now well known that respiratory ailments can be treated by the delivery to the patient of conditioned air. Such conditioning may include with the air a humidifying vapor which will serve to carry a medication deep into the lungs. In addition to moistening of the air, the air may be subjected to heating, and the treated air is then delivered through a therapeutic inhaling device directly to the user, such as by way of a face mask.

Other types of ailments can be treated using inhalation therapy. These ailments include, for example, pulmonary edema, coronary sclerosis, coronary thrombosis, bronchial asthma, pneumonia, and other afflictions. One therapeutic approach to these ailments is the administration of liquid medication to the respiratory tract of patients, whereby the liquid medication is aerosolized in a nebulizer so that the liquid medication can readily be inhaled. There are, however, a variety of problems associated with currently available nebulizer systems. One problem with such nebulizer systems is that they typically are complex and bulky. Respiration assemblies suffering from this deficiency will generally increase the discomfort of the patient.

A further problem with existing nebulizer systems is that the liquid medication will often separate from the carrier gas, which may be air or oxygen. Such a separation results in diminution of the amount of liquid medication, by an indeterminate amount, from that which was prescribed. In addition, the separated medication may be swallowed by the patient, creating the dual disadvantage of diverting medication prescribed to be inhaled and producing a substantial sudden dosage administered to the patient through the alimentary canal.

Recently, the efficacy of drugs having short half-life disappearance from beta receptor sites and peak bronchodilatation in the treatment of severe asthma is becoming evident. Such drugs, which include terbutaline and other aerosolized $\beta_2$ drugs, require frequent, and preferably continuous nebulization, if they are to be used to maximum advantage. There is a need for a therapeutic respiratory apparatus which is simple and economical and which provides a continuous controlled dosage of an aerosolized medication.

It is, therefore, an object of this invention to provide a simple and economical system for delivering aerosolized drugs to a patient.

It is another object of this invention to provide a lightweight system for delivering aerosolized drugs to a patient.

It is also an object of this invention to provide a system for delivering a continuous dosage of aerosolized drugs to a patient.

It is a further object of this invention to provide a safe system for delivering aerosolized drugs to a patient.

It is additionally an object of this invention to provide a disposable system for delivering aerosolized drugs to a patient.

It is yet a further object of this invention to provide a system for delivering aerosolized drugs to a patient, which avoids the problems associated with intermittent nebulization.

It is also another object of this invention to provide a compact system for delivering aerosolized drugs to a patient.

It is yet an additional object of this invention to provide a system for delivering aerosolized drugs to a patient, which is easy to assemble, yet effective in performing the drug delivery function.

It is a yet further object of this invention to provide a system for delivering aerosolized $\beta_2$ adrenergic drugs in a continuous dosage.

It is also a further object of this invention to provide a therapeutic respiratory apparatus which reduces the potential for diverting nebulized medication which is intended to be inhaled, to the alimentary canal.

It is additionally another object of this invention to provide a respiratory apparatus which is comfortable to the user.

A still further object of this invention is to provide a respiratory apparatus which maintains continuously a prescribed dosage of medication administered to a patient.

An additional object of this invention is to provide a respiratory apparatus which provides a visible indication of its functioning.

Yet another object of this invention is to provide a respiratory apparatus which can employ any of several commercially available nebulizer devices.

SUMMARY OF THE INVENTION

The foregoing and other objects are achieved by this invention which provides a therapeutic respiratory device of the type which delivers to a patient an aerosolized medicament in a carrier gas. In accordance with the invention, the therapeutic respiratory device is provided with a nebulizer having a medicament reservoir for the medicament, a carrier gas input port for receiving the carrier gas, and an output port for issuing a mixture of the carrier gas and the aerosolized medicament. A collapsible chamber is provided for forming a reservoir of the aerosolized medicament in the carrier gas. The collapsible chamber is arranged during use upward of the nebulizer, and is provided with an interior surface which defines the volume of the chamber. The collapsible chamber has a chamber inlet coupled to the output port of the nebulizer for receiving the mixture of the carrier gas and the aerosolized medicament. In this manner, a portion of the aerosolized medicament precipitates and drains along the interior surface to the nebulizer through the chamber inlet and the nebulizer output port and returns to the medicament reservoir. A chamber outlet issues the aerosolized medicament in the carrier gas. In addition to the foregoing, a patient coupling device is provided having an inlet for receiving the aerosolized medicament in the carrier gas from the collapsible chamber, and delivering same to the patient.

In one embodiment of the invention, the therapeutic respiratory device is provided with a one-way valve arranged between the collapsible chamber and the patient coupling device for ensuring that gas flows only outward of the collapsible chamber. The patient coupling device is preferably in the form of a mask which couples sealingly to the face of the patient. Moreover, the face mask is provided with an exhaust vent for releasing exhaled gas.

In accordance with a further embodiment of the invention, the collapsible chamber is provided with a chamber infusion input port for coupling to a medicament supply and replenishing the medicament reservoir. Preferably, the chamber infusion input port is disposed in the vicinity of the chamber inlet. In an alternative embodiment, the nebulizer is provided with the nebulizer infusion input port. In such an embodiment, the medicament reservoir is replenished directly via the infusion port.

In accordance with a further apparatus aspect of the present invention, the therapeutic respiratory device is provided with a nebulizer having an outlet for providing a continuous dosage of a medicament aerosolized in a carrier gas. There is additionally provided a chamber having an inlet for receiving the continuous dosage of the medicament aerosolized in the carrier gas and an outlet for providing a cyclically varying dosage of the medicament aerosolized in the carrier gas. The chamber has a volume which varies with the cyclically varying dosage. Additionally, a mask is provided having a mask inlet for receiving the cyclically varying dosage.

In one embodiment of the further apparatus aspect, the mask is provided with a vent for releasing exhaled gas. Also, the chamber is provided with a collapsible wall portion for producing the variation in volume. In this manner, a sufficient supply of the aerosolized medicament is available for meeting the peak demand requirement of the cyclically varying dosage. The cyclical nature of the dosage, of course, is responsive to the inhalation and exhalation by the patient. The exhaled gas is prevented from being introduced into the collapsible chamber by operation of a one-way valve arranged between the chamber and the mask for preventing gas flow from the mask to the chamber.

The nebulizer is provided with a nebulizer body having a wall portion, and as indicated, a medicament reservoir is arranged within the nebulizer body for retaining a supply of the medicament. The infusion port which supplies the medicament to the medicament reservoir is, in one embodiment, arranged to pass through the wall of the nebulizer. Alternatively, the infusion port is arranged through the wall portion of the collapsible chamber, and in the vicinity of the inlet of the chamber.

In accordance with a method aspect of the invention, the method provides for delivery of a substantially continuous dosage of an aerosolized medicament to a living being through a respiratory device. In accordance with the method aspect of the invention, the inventive method includes the step of providing a continuous flow of a carrier gas to a nebulizer having a reservoir of a predetermined medicament, and producing at an outlet of the nebulizer a continuous flow of the medicament aerosolized in the carrier gas, at a predetermined rate. The method includes the further steps of storing the aerosolized medicament in a collapsible chamber having a predetermined maximum volume and supplying the aerosolized medicament to the living being at a cyclically varying rate. The cyclically varying rate, during an inhalation portion of a cycle thereof, exceeds the predetermined rate of the continuous flow at the outlet of the nebulizer. The collapsible chamber collapses to a volume less than the predetermined maximum volume during the inhalation portion of the cycle.

In one embodiment of the method aspect of the invention, there is provided the further step of preventing gas exhaled by the living being from being supplied to the collapsible chamber. As stated herein, the reservoir of the nebulizer is replenished. Additionally, the aerosolized medicament is introduced into a mask which is coupled to the living being, at the cyclically varying rate.

DESCRIPTION OF THE DRAWING

Comprehension of the invention is facilitated by reading the following detailed description, in conjunction with the annexed drawing, in which the single figure is a plan view representation of a constant infusion breathing apparatus constructed in accordance with the principles of the invention.

DETAILED DESCRIPTION

The FIGURE illustrates a therapeutic respiratory apparatus 10 having a nebulizer 11, a collapsible chamber 12, and a mask 13. As shown, therapeutic respiratory apparatus 10 is supplied a continuous flow of a carrier gas via a gas supply line 15, which is coupled at one end to a gas supply (not shown), which, in this specific illustrative embodiment, provides a mixture of oxygen and air. The other end of gas supply line 15 is coupled to nebulizer 11 at the bottom thereof.

Nebulizer 11 is provided with a medicament reservoir 16 which contains a medicament (not shown) in liquid form. The medicament is aerosolized in the nebulizer with the carrier gas, and the resulting aerosol is issued out of a nebulizer outlet 18 to collapsible chamber 12. The aerosol is then conducted to mask 13 for delivery to the patient.

In a practical embodiment of the invention, the oxygen/air supply (not shown) may consist of respective tanks of air and oxygen which are pressurized to a typical nominal pressure of approximately 50 psi. The gas may flow into a blender and/or regulator (not shown), and then to the nebulizer at a rate on the order of 8 to 12 l/min, which is quite adequate in view of an average adult typically consuming the mixture at a rate of approximately 4 l/min.

As the patient inhales, the aerosolized medicament is drawn from collapsible chamber 12, which responsively collapses to produce a reduction in its volume. During exhalation by the patient, the flow of exhaled gases into collapsible chamber 12 is prevented by operation of a one-way valve (not shown) which may be installed in an outlet neck 19 of the collapsible chamber. In this specific illustrative embodiment, mask 13 is provided with a pair of exhaust valves 20 which serve to vent the exhaled gases into the ambient atmosphere.

Referring once again to nebulizer 11, medicament reservoir 16 is replenished by the introduction of liquid medicament into therapeutic respiratory apparatus 10. In the present arrangement, such replenishment may be achieved via an infusion port 21 which is shown to be installed in an inlet neck 22 of collapsible chamber 12. Infusion port 21 is coupled to a supply (not shown) of the medicament, and the medicament may, in certain embodiments, drip into medicament reservoir 16 at a rate on the order of 12 cc/hr. Certain embodiments of the invention will employ an infusion pump (not shown) in combination with the infusion port. It is a particular advantage of such an embodiment that numerous types of commercially available nebulizers can be employed in the system of therapeutic respiratory apparatus 10.

An optional, alternative location for infusion port 21 is shown in the figure in phantom and designated as infusion port 23. Infusion port 23 is coupled to an external supply of the liquid medicament, and possibly an infusion pump, as described hereinabove with respect to infusion port 21.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A therapeutic respiratory device of the type which delivers to a patient an aerosolized medicament in a carrier gas, the therapeutic respiratory device comprising:
    nebulizer means having a medicament reservoir for the medicament, a carrier gas input port for receiving the carrier gas, and an output port for issuing a mixture of the carrier gas and the aerosolized medicament;
    collapsible chamber means for forming a reservoir of the aerosolized medicament in the carrier gas, the collapsible chamber means being arranged during use upward of said nebulizer means and having an interior surface, said collapsible chamber means further having a chamber inlet coupled to said output port of said nebulizer means for receiving the mixture of the carrier gas and the aerosolized medicament, such that a portion of the aerosolized medicament precipitates and drains along said interior surface to said nebulizer means through said chamber inlet and said nebulizer output port and returns to said medicament reservoir, said collapsible chamber means further having a chamber outlet for issuing the aerosolized medicament in the carrier gas; and
    patient coupling means having an inlet for receiving the aerosolized medicament in the carrier gas from said collapsible chamber means, and delivering same to the patient.

2. The therapeutic respiratory device of claim 1 wherein said patient coupling means comprises mask means for coupling sealingly to the face of the patient, said face mask means being provided with exhaust vent means for releasing exhaled gas.

3. The therapeutic respiratory device of claim 1 wherein said collapsible chamber means is provided with a chamber infusion input port for coupling to a medicament supply and replenishing said medicament reservoir.

4. The therapeutic respiratory device of 3 claim wherein said chamber infusion input port is disposed in the vicinity of 5. The therapeutic respiratory device of claim 1 wherein said nebulizer means is provided with a nebulizer infusion input port for coupling to a medicament supply and replenishing said medicament reservoir.

6. A therapeutic respiratory device comprising:
    nebulizer means having an outlet for providing a continuous dosage of a medicament aerosolized in a carrier gas; variable volume chamber means having an interior surface, an inlet for receiving said continuous dosage of said medicament aerosolized in said carrier gas, and an outlet for providing a cyclically varying dosage of said medicament aerosolized in said carrier gas, the volume of said chamber means with said cyclically varying dosage; and said nebulizer means and said chamber means being arranged such that a portion of the aerosolized medicament precipitates and drains along said interior surface to said nebulizer outlet
    mask means having a mask inlet for receiving said cyclically varying dosage.

7. The therapeutic respiratory device of claim 6 wherein said mask means is provided with vent means for releasing exhaled gas.

8. The therapeutic respiratory device of claim 6 wherein said chamber means is provided with a collapsible wall portion for producing said variation in volume.

9. The therapeutic respiratory device of claim 6 wherein said nebulizer means is provided with a nebulizer body having a wall portion, and a medicament reservoir arranged within said nebulizer body for retaining a supply of said medicament.

10. The therapeutic respiratory device of claim 9 wherein there is further provided infusion port means for supplying said medicament to said reservoir means.

11. The therapeutic respiratory device of claim 10 wherein said infusion port means is arranged through said wall portion of said nebulizer body.

12. The therapeutic respiratory device of claim 10 wherein said infusion port means is arranged in the vicinity of said inlet of said chamber means.

* * * * *

UNITED STATES PATENT AND TRADEMARK OFFICE
CERTIFICATE OF CORRECTION

PATENT NO. : 4,865,027

DATED : September 12, 1989

INVENTOR(S) : Craig Van Laanen and Frank W. Moler

It is certified that error appears in the above-identified patent and that said Letters Patent is hereby corrected as shown below:

Cover page, line [75] Inventors, change "Craig Laanen" to -- Craig Van Lannen --;

Col. 1, line 60, change "$\frac{1}{2}$2" to -- $\frac{1}{2}$ --;

Claim 4, line 3, after "of" insert -- said chamber inlet.";

Claim 6, line 10, after "means" insert -- varying --; and

Claim 6, line 14, after "outlet" insert -- ; and --.

Signed and Sealed this

Ninth Day of October, 1990

Attest:

HARRY F. MANBECK, JR.

*Attesting Officer*  *Commissioner of Patents and Trademarks*